United States Patent
Kang et al.

(10) Patent No.: US 6,709,450 B2
(45) Date of Patent: Mar. 23, 2004

(54) BLOOD VESSEL GRAFT AND GRAFT INTRODUCER

(75) Inventors: Sung-Gwon Kang, Seoul (KR); Eun-Sang Kim, Seoul (KR)

(73) Assignee: S & G Biotech, Inc., Seoul (KR)

( * ) Notice: Subject to any disclaimer, the term of this patent is extended or adjusted under 35 U.S.C. 154(b) by 0 days.

(21) Appl. No.: 09/958,464

(22) PCT Filed: Feb. 7, 2001

(86) PCT No.: PCT/KR01/00179
§ 371 (c)(1),
(2), (4) Date: Feb. 19, 2002

(87) PCT Pub. No.: WO01/56501
PCT Pub. Date: Aug. 9, 2001

(65) Prior Publication Data
US 2003/0158594 A1 Aug. 21, 2003

(30) Foreign Application Priority Data
Feb. 7, 2000 (KR) .......................................... 2000/5568
Feb. 29, 2000 (KR) ........................................ 2000/10168

(51) Int. Cl.⁷ ................................................. A61F 2/06
(52) U.S. Cl. ..................................... 623/1.13; 623/1.23
(58) Field of Search .............................. 623/1.11–1.19, 623/1.23, 1.36, 1.51, 1.52, 1.53, 1.54; 606/191, 194, 198

(56) References Cited

U.S. PATENT DOCUMENTS

| 5,383,892 A | * | 1/1995 | Cardon et al. | 623/1.16 |
| 5,769,887 A | * | 6/1998 | Brown et al. | 623/1.23 |
| 5,817,126 A | * | 10/1998 | Imran | 623/1.15 |
| 5,916,263 A | * | 6/1999 | Goicoechea et al. | 623/1.11 |
| 6,102,940 A | * | 8/2000 | Robichon et al. | 623/1.35 |
| 6,123,723 A | * | 9/2000 | Konya et al. | 623/1.11 |
| 6,152,956 A | * | 11/2000 | Pierce | 623/1.13 |
| 6,187,036 B1 | * | 2/2001 | Shaolian et al. | 623/1.15 |
| 6,287,335 B1 | * | 9/2001 | Drasler et al. | 623/1.28 |
| 6,395,019 B2 | * | 5/2002 | Chobotov | 623/1.13 |
| 6,432,127 B1 | * | 8/2002 | Kim et al. | 623/1.11 |
| 6,508,835 B1 | * | 1/2003 | Shaolian et al. | 623/1.35 |

FOREIGN PATENT DOCUMENTS

| EP | 0809980 A | 12/1997 | | |
| WO | WO 9614808 A1 | * | 5/1996 | ............. A61F/2/02 |
| WO | WO 9939662 A | 8/1999 | | |

* cited by examiner

*Primary Examiner*—Michael J. Milano
*Assistant Examiner*—Jessica R Baxter
(74) *Attorney, Agent, or Firm*—Blakely, Sokoloff, Taylor & Zafman (57) ABSTRACT

Disclosed are a blood vessel graft and a graft introducer, the graft having a main body and first and second stents each mounted on an end of the main body, the graft introducer including an insertion tube member in which the blood vessel graft main body and the first stent member are inserted in a state where they are contracted, a first pusher member into which the second stent member is inserted in a state where it is contracted, the first pusher member being movably inserted into the insertion tube member to push the first stent member and the blood vessel graft main body out of the insertion tube member, and a second pusher member in which a catheter passing through the introducer is inserted, the second pusher member being movably inserted into the pusher member to push the second stent member inserted in the first pusher member out of the insertion tube member, thereby disposing the blood vessel graft in the blood vessel.

9 Claims, 6 Drawing Sheets

BLOOD VESSEL GRAFT AND GRAFT INTRODUCER

This is a non-provisional application claiming the benefit of International application number PCT/KR01/00179 filed Feb. 7, 2001.

BACKGROUND OF THE INVENTION AND PRIOR ART (a) Field of the Invention

The present invention relates to a blood vessel graft and a graft introducer, and more particularly, to a graft introducer that can easily guide a blood vessel graft into a blood vessel, and to such a blood vessel graft that is reduced in its diameter when it is contracted, thereby making it possible to minimize inner and outer diameters of the introducer so that the introducer can be easily inserted into the weakened blood vessel.

(b) Description of the Related Art

As an example, an aneurysm is an abnormal blood-filled dilatation of a blood vessel, and especially an artery, resulting from disease of the vessel wall. It is a very dangerous malady, such that the vessel wall may be broken when the blood pressure within the blood vessel is increased above a predetermined level.

Such an aneurysm is generally cured through a surgical operation. However, for a patient to whom the surgical operation cannot be applied, a blood vessel graft has been developed. But since an introducer for locating the graft in the blood vessel has a diameter larger than 6 mm, the blood vessel should be locally opened through surgery, potentially causing complications. Furthermore, if the blood vessel is complicatedly curved, it is very difficult to dispose the graft in the blood vessel. Therefore, a punching operation method has been developed and used.

In the punching operation method, a surgical operation for opening the blood vessel is not performed, but a minute hole is formed in the artery, and the introducer is inserted into the artery through the minute hole. The blood vessel graft is then disposed in the weakened blood vessel by way of the introducer.

To use such a punching operation method, it is required that the inner and outer diameters of the graft introducer be less than, for example, 4 mm and 4.5 mm, respectively. In addition, the diameter of the graft when it is contracted should be less than the inner diameter of the introducer so that it can be inserted into the introducer.

The conventional graft introducer includes an insertion tube into which the blood vessel graft is inserted, and a pusher for pushing the inserted graft out of the insertion tube. The blood vessel graft includes a graft main body that is introduced into the blood vessel, and self-expandable stents mounted inside of each end of the main body to maintain the shape of the blood vessel when it is disposed in the blood vessel.

However, in the conventional blood vessel graft, since the self-expandable stents are each mounted inside an end of the main body, the graft main body and the stents overlap, increasing the diameter of the graft when it is contracted. This results in increasing inner and outer diameters of the introducer into which the blood vessel graft is inserted.

SUMMARY OF THE INVENTION

The present invention has been made in an effort to solve the above described problems, and it is an object of the present invention to provide a graft introducer that can easily guide a blood vessel graft into a blood vessel, and to such a blood vessel graft that is reduced in its diameter when it is contracted, thereby making it possible to minimize inner and outer diameters of the introducer so that the introducer can be easily inserted into the weakened blood vessel.

To achieve the above object, the present invention provides a blood vessel graft having a front side and a rear side in a lengthwise direction, the blood vessel graft comprising:

a flexible blood vessel graft main body to be disposed within a blood vessel to prevent blood pressure from being applied to a weakened blood vessel, the flexible blood vessel graft main body having a front end and a rear end;

a first stent member having a front end and a rear end, the rear end of the first stent member being connected to the front end of the flexible blood vessel graft main body with a gap between the rear end of the first stent member and the front end of the flexible blood vessel graft main body to avoid overlapping the blood vessel graft main body and the first stent member; and a second stent member having a front end and a rear end, the front end of the second stent member being connected to the rear end of the flexible blood vessel main body with a gap between the front end of the second stent member and the rear end of the flexible blood vessel main body to avoid overlapping the blood vessel graft main body and the second stent member.

Preferably, the first stent member has an identical structure to that of the second stent member. A diameter of the second stent member when the second stent member is contracted is smaller than that of the first stent member.

Each of the first and second stent members comprise a plurality of reference turns each having a unit member which has a zigzag shape, and having a plurality of straight sections and a plurality of bending points that are interlocked with those of an adjacent reference turn so as to provide a mesh-structure. Each of the first and second stent members further comprise an overlapped member twisted along the straight sections.

The second stent member is formed of a wire having a diameter of less than that of the first stent member. The first and second stent members are connected to each other by connecting bars, each of the connecting bars being formed of wires twisted with each other more than twice.

The rear end of the first stent member is connected to the front end of the flexible blood vessel graft main body by a connecting member, and the gap between the rear end of the first stent member and the front end of the flexible blood vessel graft main body is over a predetermined length of about 3 mm.

The front end of the second stent member is connected to the rear end of the flexible blood vessel main body by a connecting member, and the gap between the front end of the second stent member and the rear end of the flexible blood vessel main body is over a predetermined length of about 3 mm.

According to another aspect, the present invention provides a graft introducer for disposing a blood vessel graft in a blood vessel, the blood vessel graft having a main body and first and second stents, each connected to an end of the main body, the graft introducer comprising:

an insertion tube member into which the blood vessel graft main body and the first stent member are inserted in a state where they are contracted;

a first pusher member into which the second stent member is inserted in a state where it is contracted, the first pusher member being movably inserted into the insertion tube member to push the first stent member and the blood vessel graft main body out of the insertion tube member; and a second pusher member into which a catheter passing through the introducer is inserted, the second pusher member being movably inserted into the first pusher member to push the second stent member inserted in the first pusher member out of the insertion tube member, thereby disposing the blood vessel graft in the blood vessel.

The insertion tube member is formed having an outer diameter of less than 4.7 mm and an inner diameter of less than 4 mm so that it can be easily inserted in the blood vessel, and the blood vessel stent and the first pusher member can be easily inserted therein.

The first pusher member is formed having an outer diameter of less than 3.9 mm and an inner diameter of less than 3.4 mm so that it can be easily inserted into the insertion tube member, and the second stent member can be easily inserted therein.

The second pusher member is formed having an outer diameter of less than 2.9 mm and an inner diameter of less than 1.6 mm and is made of a hard material so as to be movable in the first pusher member and to be easily pushed toward a front end of the insertion tube member.

DETAILED DESCRIPTION OF THE PREFERRED EMBODIMENTS

A preferred embodiment of the present invention will be described in more detail with reference to the accompany drawings.

Figure 1:
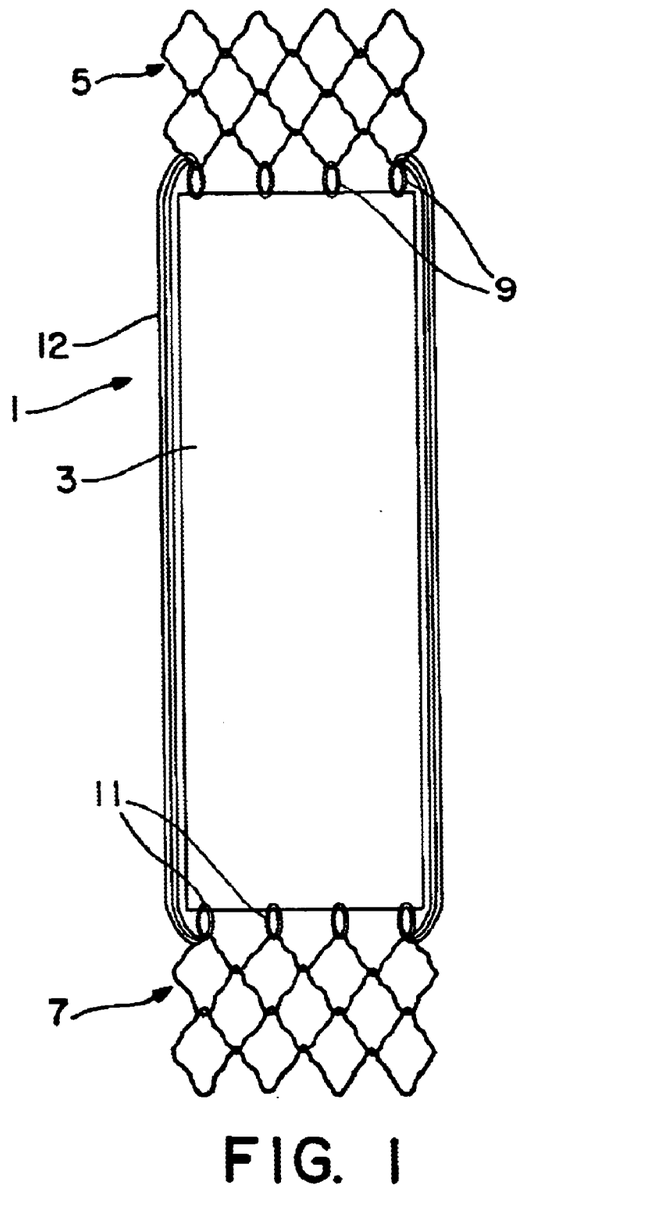
FIG. 1 is a front view of a blood vessel graft according to the present invention.

Referring first to FIG. 1, the inventive blood vessel graft 1 of the present invention comprises a blood vessel graft main body 3 for preventing blood pressure from being applied to a weakened blood vessel, the blood vessel graft main body 3 being at least partly cylindrical and flexible;

a first stent member 5 connected to a first end of the blood vessel graft main body 3, the first stent member 5 being contractible to a predetermined size and self-expandable so as to support the blood vessel graft main body 3; and a second stent member 7 connected to a second end of the blood vessel graft main body 3, the second stent member 7 being contractible to a predetermined size of less than that of the first stent member 5 when it is contracted, and self-expandable to a predetermined level so as to support the blood vessel graft main body 3.

The first and second stent members 5 and 7 are identical to each other, but made of wires having different diameters.

Figure 6:
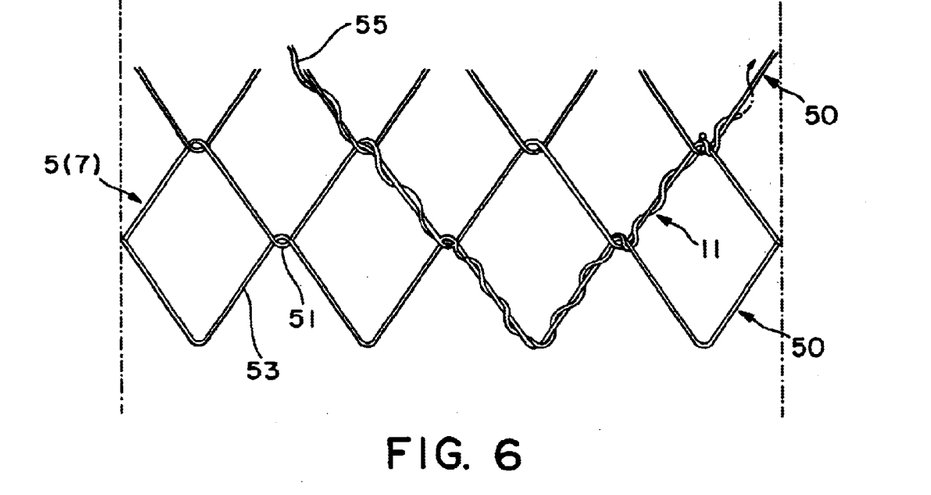
FIG. 6 is a detailed view of a stent member depicted in FIG. 1.

Describing in more detail, as shown in FIG. 6, the stent member 5 (or 7) comprises a plurality of reference turns 50 each having a zigzag shape with a plurality of bending points 51 that are interlocked with those of the adjacent reference turn and a plurality of straight sections 53 so as to provide a mesh-structure; and an overlap member overlapped on the straight sections by being twisted along the straight sections.

The first stent member 5 is connected to the first end of the blood vessel graft main body 3 by first connecting members 9. Preferably, the first stent member 5 is formed of a wire having a predetermine diameter (i.e., 0.22 mm) so as to provide a predetermined expansive power.

It is further preferable that the first stent member 5 is connected to the blood vessel graft main body 3 by the first connecting members 9 such that a gap therebetween in a lengthwise direction of the graft 1 is over a predetermined length of about 3 mm so as to avoid overlapping the blood vessel graft main body and the first stent member 5.

The second stent member 7 is made in the same manner as that used for making the first stent member 5, and is formed of a wire having a predetermined diameter of less than 0.21 mm so that the diameter when it is contracted is less than that of the first stent member 5. The second stent member 7 is connected to the blood vessel graft main body 3 by second connecting members 11.

It is preferable that the second stent member 7 is connected to the blood vessel graft main body 3 by the second connecting members 11 such that a gap therebetween in a lengthwise direction of the graft 1 is over a predetermined length of about 3 mm so as to avoid overlapping the blood vessel graft main body and the first stent member.

In addition, the first and second stent members 5 and 7 are connected to each other by a plurality of connecting bars 12 disposed on an outer side of the blood vessel graft main body 3.

The connecting bars 12 are made of the same material (i.e., nitinol) as that used for the first and second stent members 5 and 7, or a different material (i.e., stainless steel) having a similar property. Each of the connecting bars 12 is made of a plurality of wires twisted with each other more than twice. The connecting bars 12 are connected to the first and second stent members 5 and 7 by being twisted onto the same more than once.

The connecting bars 12 are provided to prevent the first stent member 5 from being moved toward the second stent member 7 by the blood pressure when the blood vessel graft main body 3 is expanded after the graft is disposed into the weakened blood vessel, and the blood vessel graft main body 3 is expanded.

FIGS. 2 to 5 show a graft introducer according to the present invention, which is used to dispose the graft 1 in the weakened blood vessel wall.

The inventive graft introducer is preferably formed such that outer and inner diameters thereof are less than predetermined levels.

As shown in the drawings, the inventive graft introducer comprises an insertion tube member 13 in which the blood vessel graft main body 3 and the first stent member 5 are inserted in a state where they are contracted; a first pusher member 15 in which the second stent member 7 is inserted in a state where it is contracted, the first pusher member 15 being movably inserted into the insertion tube member 13 to push the first stent member 5 and the blood vessel graft main body 3 out of the insertion tube member 13; and a second pusher member 19 in which a catheter 17 passing through the introducer is inserted, the second pusher member 19 being movably inserted into the first pusher member 15 to push the second stent member 7 inserted in the first pusher member 15 out of the insertion tube member 13, thereby disposing the blood vessel graft 1 in the blood vessel.

Figure 2:
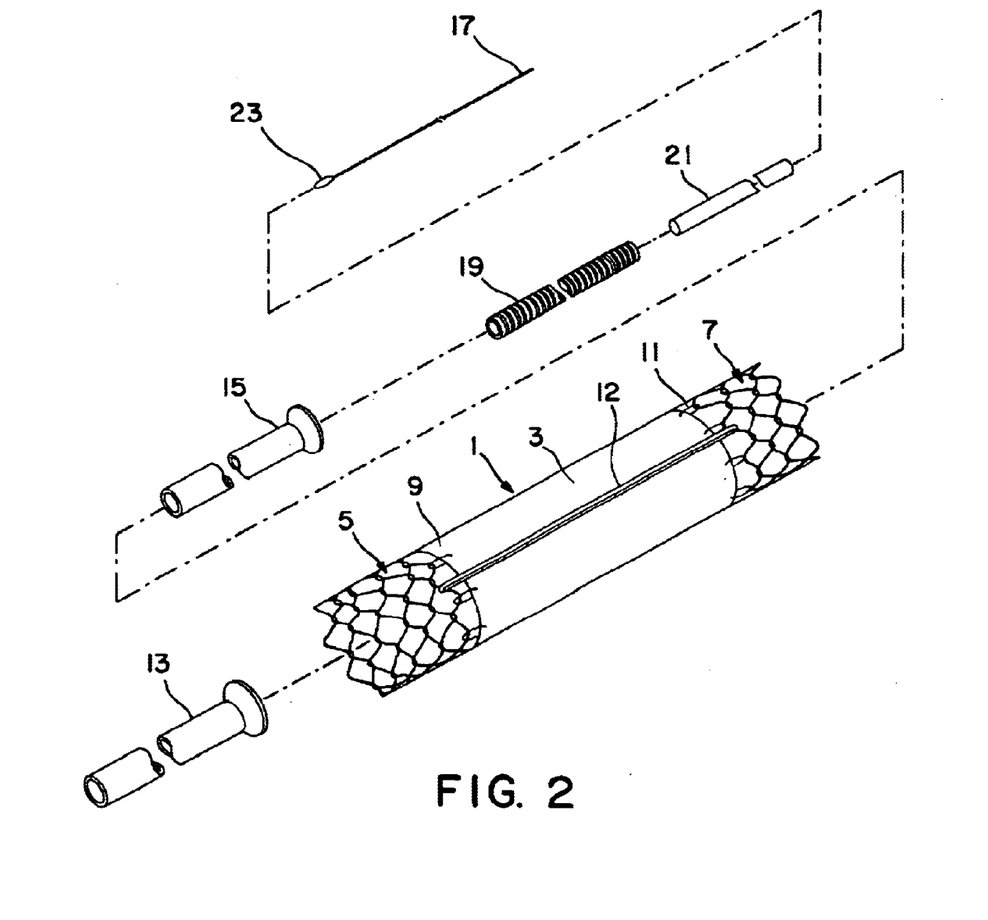
FIG. 2 is an exploded perspective view of a graft introducer according to the present invention.

Preferably, the insertion tube member 13 is formed having an outer diameter of less than 4.7 mm and an inner diameter of less than 4 mm so that it can be easily inserted in the blood vessel, and so the blood vessel graft 1 and the first pusher member 15 can be easily inserted therein.

In addition, it is preferable that the first pusher member 15 is formed having an outer diameter of less than 3.9 mm and an inner diameter of less than 3.4 mm so that it can be easily inserted into the insertion tube member 13, and so the second stent member 7 can be easily inserted therein.

It is further preferable that the insertion tube member 13 and the first pusher member 15 are made of synthetic resins such as Teflon so that the graft 1 can be easily disposed therein.

The second pusher member 19 is formed having an outer diameter of less than 2.9 mm and an inner diameter of less than 1.6 mm. The second pusher member 19 is made by coiling a metal such as iron or steel, a non-ferrous metal such as aluminum, or a hard metal such as alloy steel.

In addition, a reinforcing member 21 having a predetermined length is disposed inside the second pusher member 19 to enhance the rigidity of the second pusher member 19. The reinforcing member 21 may be made of any material such as synthetic resins, a metal, and a nonmetal that can enhance the rigidity.

The guider-passing catheter 17 is designed having an outer diameter of less than 1.3 mm and an inner diameter of less than 1 mm, and is provided at its front end with a tip portion 23 for guiding the guider. The tip portion 23 is designed having an outer diameter of less than 4 mm.

The procedure for locating the blood vessel graft in the blood vessel using the graft introducer will be described hereinafter.

First, as shown in FIG. 1, after the guider-passing catheter 17 is inserted into the insertion tube member 5 and the first pusher member 15, the rear end of the insertion tube member 13 is disposed to oppose the front end of the first pusher member 15.

Figure 3:
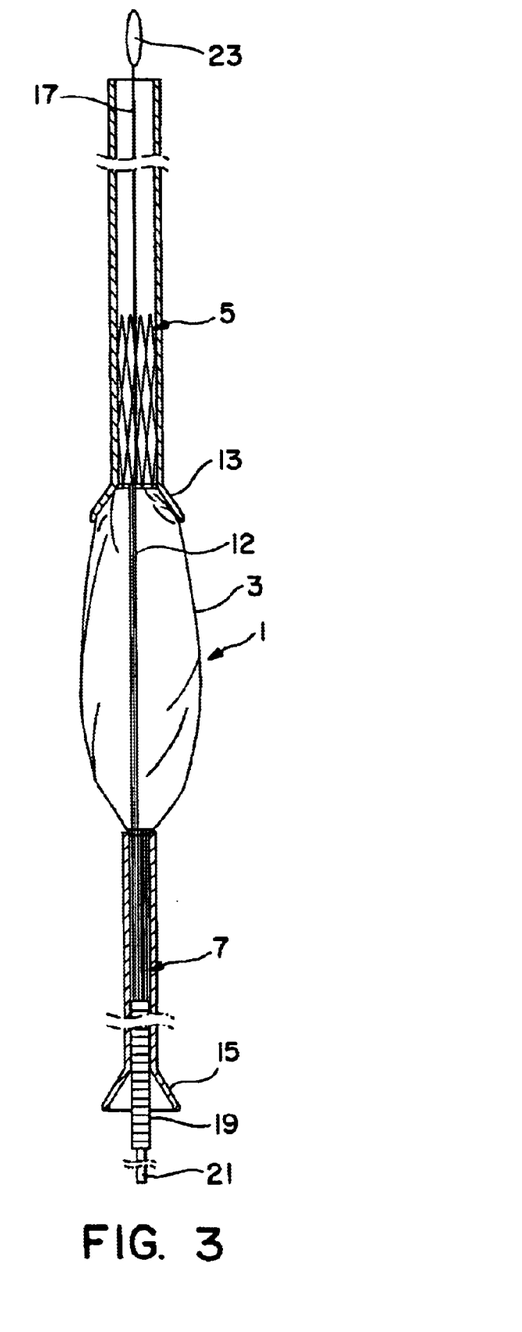
FIG. 3 is a view illustrating a using state of a blood vessel graft and a graft introducer, in which the blood vessel graft is inserted into a part of the introducer.

Then, as shown in FIG. 3, the second stent member 7 is inserted into the first pusher member 15 through the front end thereof in a state where it is contracted. Next, the first stent member 5 and the blood vessel graft main body 3 are inserted through the rear end of the insertion tube member 13.

Figure 4:
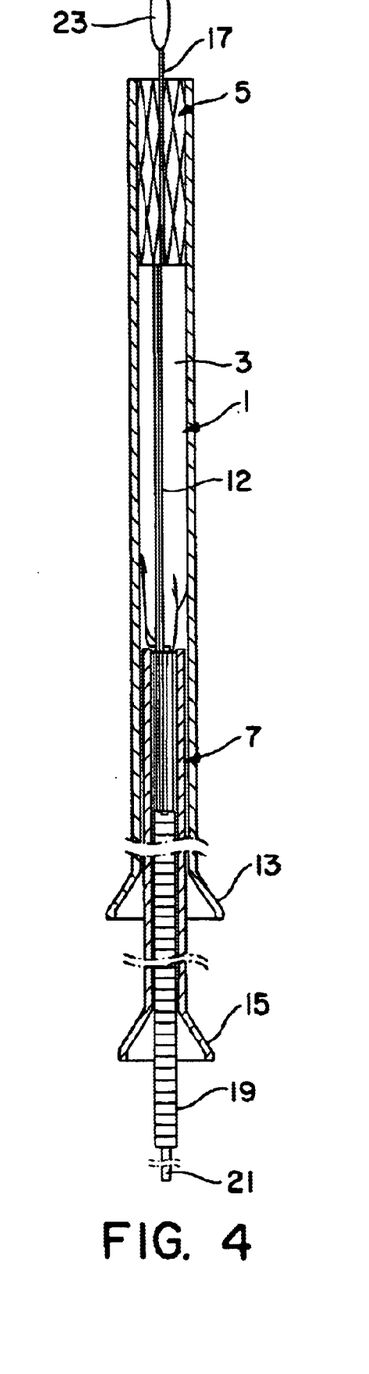
FIG. 4 is a view illustrating a using state of a blood vessel graft and a graft introducer, in which the blood vessel graft is completely inserted into the introducer.

In this state, the first pusher member 15 is inserted into the rear end of the insertion tube member 13 after which the first pusher member 15 is pushed toward the front end of the insertion tube member 13 or the insertion tube member 13 is pulled toward the first pusher member 15 in a state where the first pusher member 15 is fixed. As a result, the first pusher member 15 pushes the blood vessel graft main body 3 toward the front end of the insertion tube member 13 and the first stent member 5 is located on the front end of the insertion tube member 13 as shown in FIG. 4.

As described above, in a state where the blood vessel graft 1 is disposed in the first pusher member 15 and the insertion tube member 13, the insertion tube member 13 is inserted in the weakened blood vessel of the patient using a guide member inserted in the guider-passing catheter 17.

Figure 5:
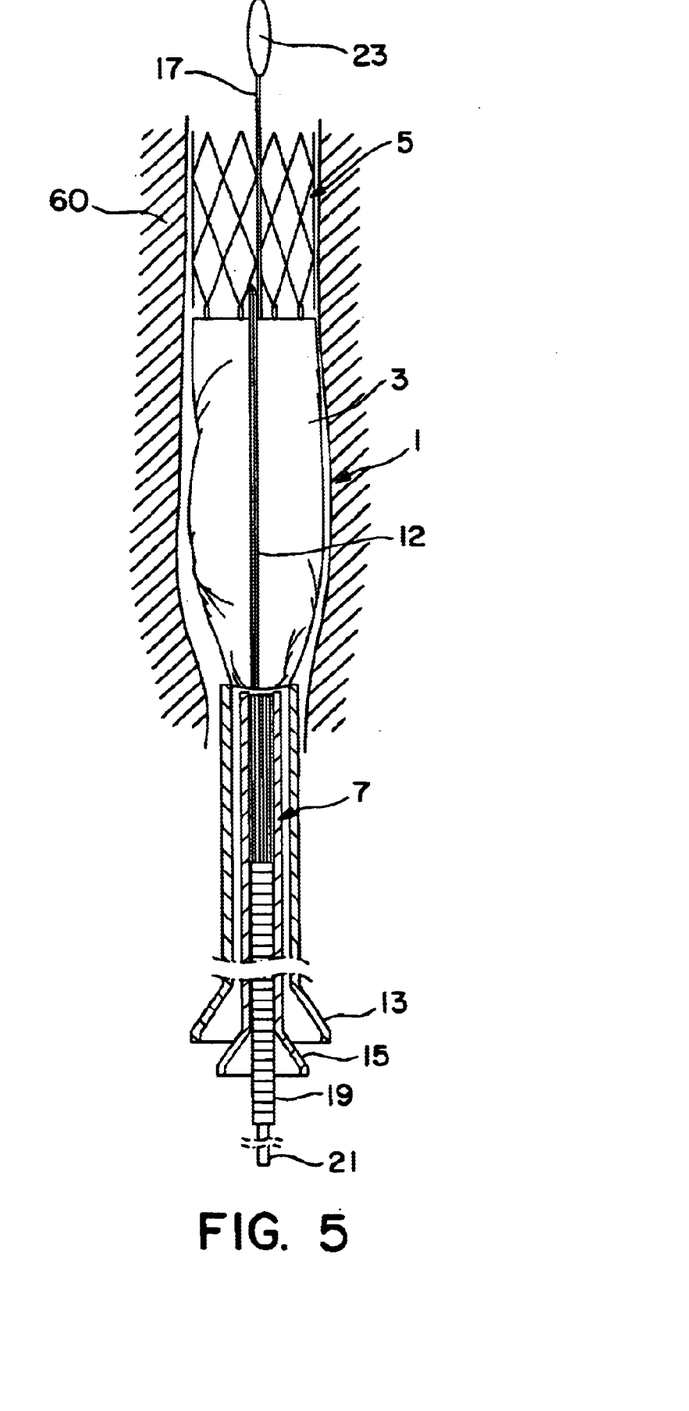
FIG. 5 is a view illustrating a using state of a blood vessel graft and a graft introducer, in which the blood vessel graft is being expelled from the introducer.

In this state, when the first pusher member 15 is pushed up to the front end of the insertion tube member 13, the first stent member 5 and the blood vessel graft main body 3 are moved out of the insertion tube member 13, thereby disposing the first stent member 5 and the blood vessel graft main body 3 on the blood vessel 60 as shown in FIG. 5.

After the above, in a state where the first pusher member 15 is moved up to the front end of the insertion tube member 13, the second pusher member 19 is pushed forward to move the second stent member 7 out of the first pusher member 15, and so the second stent member 7 is disposed in the blood vessel. Accordingly, the blood vessel graft 1 is disposed in the blood vessel 60.

As described above, since the diameter of the introducer is minimized, the blood vessel graft can be easily disposed in the blood vessel. The graft can be supported without using a special support and can be easily inserted into or withdrawn from the blood vessel, providing convenience to the user.

What is claimed is:

1. A blood vessel graft having a front side and a rear side in a lengthwise direction, the blood vessel graft comprising:
    a flexible blood vessel graft main body to be disposed within a blood vessel to prevent blood pressure from being applied to a weakened blood vessel, the flexible blood vessel graft main body having a front end and a rear end;
    a first stent member having a front end and a rear end, the rear end of the first stent member being connected to the front end of the flexible blood vessel graft main body with a gap between the rear end of the first stent member and the front end of the flexible blood vessel graft main body to avoid overlapping the blood vessel graft main body and the first stent member; and
    a second stent member having a front end and a rear end, the front end of the second stent member being connected to the rear end of the second stent member and the rear end of the flexible blood vessel main body to avoid overlapping the blood vessel graft main body and the second stent member, wherein the first and second stent members are connected to each other by connecting bars, each of the connecting bars being formed of wires twisted with each other more than twice.

2. A blood vessel graft of claim 1 wherein the first stent member has an identical structure to that of the second stent member.

3. A blood vessel graft of claim 1 wherein a diameter of the second stent member when the second stent member is contracted is smaller than that of the first stent member.

4. A blood vessel graft of claim 1 wherein each of the first and second stent members comprise a plurality of reference turns each having a unit member which has a zigzag shape, a plurality of straight sections and a plurality of bending points that are interlocked with those of an adjacent reference turn so as to provide a mesh-structure.

5. A blood vessel graft of claim 4 wherein each of the first and second stent members further comprise an overlapped member twisted along the straight sections.

6. A blood vessel graft of claim 1 wherein the second stent member is formed of a wire having a diameter of less than that of the first stent member.

7. A blood vessel graft of claim 1 wherein the rear end of the first stent member is connected to the front end of the flexible blood vessel graft main body by a connecting member, and the gap between the rear end of the first stent member and the front end of the flexible blood vessel graft main body is over a predetermined length of about 3 mm.

8. A blood vessel graft of claim 1 wherein the front end of the second stent member is connected to the rear end of the flexible blood vessel main body by a connecting member, and the gap between the front end of the second stent member and the rear end of the flexible blood vessel main body is over a predetermined length of about 3 mm.

9. A graft introducer for disposing a blood vessel graft in a blood vessel, the blood vessel graft having a main body and first and second stents each connected to an end of the main body, the graft introducer comprising:

an insertion tube member into which the blood vessel graft main body and the first stent member are inserted in a state where they are contracted, wherein the insertion tube member includes an outer diameter of less than 4.7 mm and an inner diameter of less than 4 mm so that it can be easily inserted in the blood vessel, and the blood vessel stent and the first pusher member can be easily inserted therein;

a first pusher member into which the second stent member is inserted in a state where it is contracted, the first pusher member being movably inserted into the insertion tube member to push the first stent member and the blood vessel graft main body out of the insertion tube member, wherein the first pusher member includes an outer diameter of less than 3.9 mm and an inner diameter of less than 3.4 mm so that it can be easily inserted into the insertion tube member, and the second stent member can be easily inserted therein; and a second pusher member into which a catheter passing through the introducer is inserted, the second pusher member being movably inserted into the first pusher member to push the second stent member inserted in the first pusher member out of the insertion tube member, thereby disposing the blood vessel graft in the blood vessel, wherein the second pusher member includes an outer diameter of less than 2.9 mm and an inner diameter of less than 1.6 mm and is made of a hard material so as to be movable in the first pusher member and to be easily pushed toward a front end of the insertion tube member.

* * * * *